United States Patent
Doetz et al.

(10) Patent No.: US 9,231,215 B2
(45) Date of Patent: Jan. 5, 2016

(54) PHENACENE COMPOUNDS FOR ORGANIC ELECTRONICS

(71) Applicant: BASF SE, Ludwigshafen (DE)

(72) Inventors: Florian Doetz, Mannheim (DE); Thomas Weitz, Mannheim (DE); Jiao Chongjun, Singapore (SG); Hiroyoshi Noguchi, Nishinomiya (JP); Ang Sweemeng, Singapore (SG); Mi Zhou, Singapore (SG); Doi Iori, Singapore (SG); Ashok Kumar Mishra, Singapore (SG)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/399,756

(22) PCT Filed: Apr. 29, 2013

(86) PCT No.: PCT/IB2013/053379
§ 371 (c)(1),
(2) Date: Nov. 7, 2014

(87) PCT Pub. No.: WO2013/168048
PCT Pub. Date: Nov. 14, 2013

(65) Prior Publication Data
US 2015/0126751 A1   May 7, 2015

Related U.S. Application Data

(60) Provisional application No. 61/643,358, filed on May 7, 2012.

(30) Foreign Application Priority Data

May 7, 2012   (EP) .................................. 12166922

(51) Int. Cl.
| H01L 51/00 | (2006.01) |
| C07D 333/52 | (2006.01) |
| C07D 333/72 | (2006.01) |
| C07D 209/86 | (2006.01) |
| C07D 307/78 | (2006.01) |
| C07D 307/87 | (2006.01) |
| C07D 495/04 | (2006.01) |
| H01L 51/42 | (2006.01) |
| H01L 51/50 | (2006.01) |
| H01L 51/05 | (2006.01) |

(52) U.S. Cl.
CPC .......... *H01L 51/0074* (2013.01); *C07D 209/86* (2013.01); *C07D 307/78* (2013.01); *C07D 307/87* (2013.01); *C07D 333/52* (2013.01); *C07D 333/72* (2013.01); *C07D 495/04* (2013.01); *H01L 51/0508* (2013.01); *H01L 51/42* (2013.01); *H01L 51/5012* (2013.01); *H01L 51/0545* (2013.01); *Y02E 10/549* (2013.01)

(58) Field of Classification Search
CPC .................................................... H01L 51/0074
USPC ............................................................ 549/41
See application file for complete search history.

(56) References Cited

U.S. PATENT DOCUMENTS

| 2006/0202195 A1 | 9/2006 | Marks et al. |
| 2007/0181961 A1 | 8/2007 | Marks et al. |
| 2011/0049485 A1* | 3/2011 | Kim et al. ........................ 257/40 |
| 2011/0253944 A1 | 10/2011 | Han et al. |

FOREIGN PATENT DOCUMENTS

| GB | 1 027 577 | 4/1996 |
| JP | 2009-63846 | 3/2009 |

OTHER PUBLICATIONS

Majetich et al., Heterocyclics (2007), vol. 72, pp. 157-161.*
King, Med. Chem., Principle and Practice (1994), pp. 206-208.*
International Search Report issued Oct. 3, 2013 in PCT/IB13/053379 filed Apr. 29, 2013.

* cited by examiner

*Primary Examiner* — Taofiq A Solola
(74) *Attorney, Agent, or Firm* — Oblon, McClelland, Maier & Neustadt, L.L.P.

(57) ABSTRACT

Phenacene compounds of formula (I) are disclosed. All the variables in the formula are the same as defined in the description. A thin film semiconductor comprising the above compounds, and a field effect transistor device, a photovoltaic device, an organic light emitting diode device and a unipolar or complementary circuit device comprising the thin film are also disclosed.

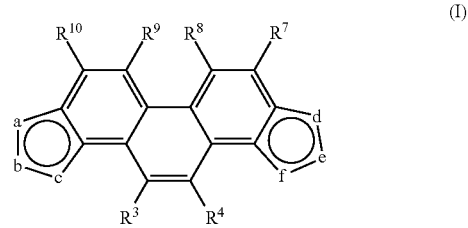

(I)

17 Claims, 3 Drawing Sheets

PHENACENE COMPOUNDS FOR ORGANIC ELECTRONICS

Figure 1A:
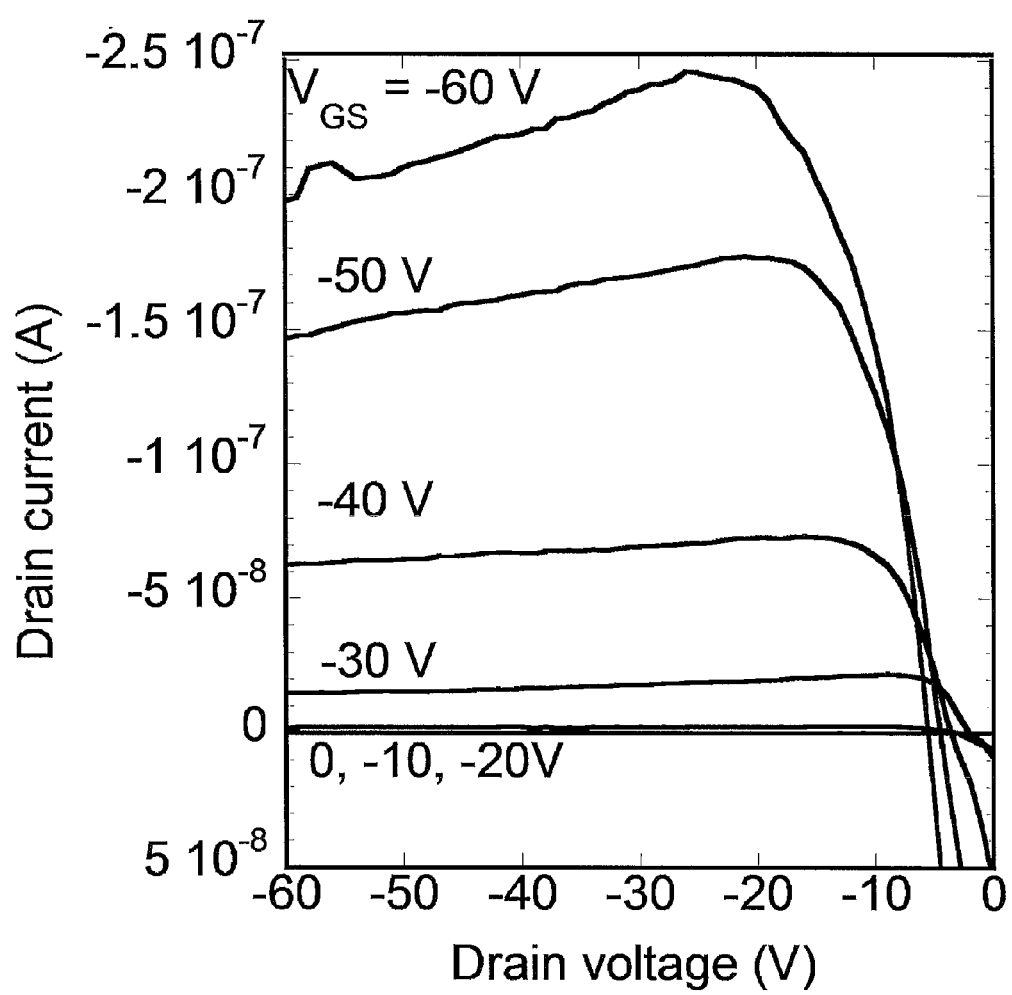

The invention relates to phenacene compounds and their use.

Organic semiconducting materials can be used in electronic devices such as organic photovoltaic (OPV) cells, organic field-effect transistors (OFETs) and organic light emitting diodes (OLEDs).

It is desirable that the organic semiconducting materials are compatible with liquid processing techniques such as spin coating, solution casting or printing. Liquid processing techniques are convenient from the point of processability, and can also be applied to plastic substrates. Thus, organic semiconducting materials which are compatible with liquid processing techniques allow the production of low cost, light weight and, optionally also flexible, electronic devices, which is a clear advantage of these organic semiconducting materials compared to inorganic semiconducting materials.

Furthermore, it is desirable that the organic semiconducting materials are stable, in particular towards oxidation.

When used in organic field-effect transistors (OFETs), the organic semiconducting materials should show a high charge carrier mobility and a high on/off ratio.

The use of organic semiconducting materials in electronic devices, in particular in organic field effect transistors (OFETs) is known in the art.

Okamoto, K.; Kawasaki, N.; Kaji, Y.; Kubozono, Y.; Fujiwara, A.; Yamaji, M. *J. Am. Chem. Soc.* 2008, 130, 10470-10471 and Kawasaki, N.; Kubozono, Y.; Okamoto, H.; Fujiwara, A.; Yamaji, M. *Appl. Phys. Lett.* 2009, 94, 043310 describe picene

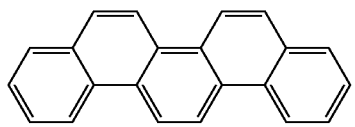 [SMILES: c1ccc2c(c1)ccc1c2ccc2c3ccccc3ccc21]

for vacuum-deposited OFETs with a charge carrier mobility approaching 3 $cm^2V^{-1} s^{-1}$.

JP2009/063846 discloses alkylated picene as solution-based OFET with a charge carrier mobility of up to 2 $cm^2V^{-1} s^{-1}$.

S. Shinamura et al., K. J. Am. Chem. Soc. 2011, 133, 5024-5035 disclose linear- and angular-shaped naphthodithiophenes of the following formula:

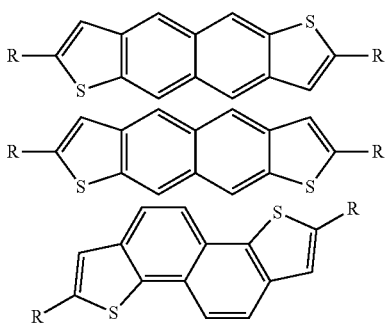

wherein R is H, n-$C_8H_{17}$ or phenyl,
for vacuum-deposited OFET with a charge carrier mobility approaching 1.5 $cm^2/V$ s.

J. Gao et al., Adv. Mater. 2007, 19, 3008-3011 disclose dibenzothienodithiophene

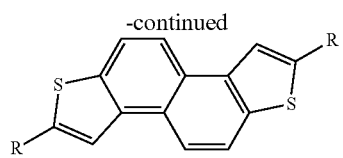

for FET with a charge carrier mobility above 0.5 $cm^2 V^{-1} s^{-1}$ and an on/off ratio greater than $10^6$.

K. Xiao et al., J. Am. Chem. Soc. 2005, 127, 13281-13286 disclose pentathienoacene

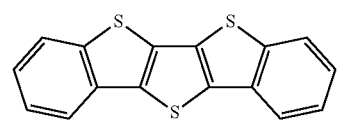 [SMILES: c1ccc2c(c1)sc1c2sc2c3ccccc3sc21]

with a charge carrier mobility of 0.045 $cm^2V^{-1} s^{-1}$ and an on/off ratio of $10^3$ for vacuum-deposited OFET.

J. Wang et al., Chem. Mater. 2009, 21, 2595-2597, describe the following small molecule:

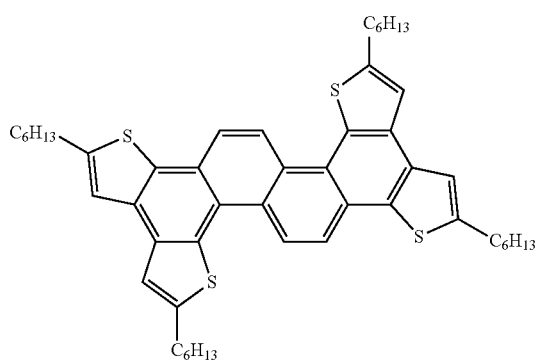

for vacuum-deposited OFET with a charge carrier mobility up to 0.4 $cm^2/V$ s.

Accordingly, given potential applications in inexpensive and large-area organic electronics that can be produced by high-throughput reel-to-reel manufacture, the art desires new organic p-type semiconducting compounds, especially those possessing desirable properties such as air stability, high charge transport efficiency, and good solubility in common organic solvents.

In light of the foregoing, it is an object of the present invention to provide compounds that can be utilized as organic semiconductors and related materials, compositions, composites, and/or devices that can address various deficiencies and shortcomings of the state-of-the-art, including those outlined above.

The object is solved by phenacene compounds of formula I:

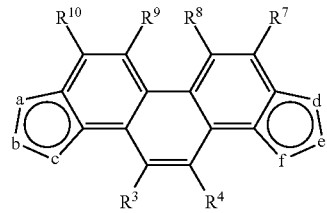

wherein
one of groups a, b and c is X and the other two groups are C—R¹ and C—R², respectively, one of groups d, e and f is X and the other two groups are C—R⁵ and C—R⁶, respectively, wherein X are, independently of each other, selected from the group consisting of NH, O, S and Se, preferably selected from the group consisting of O, S and Se, more preferably selected from the group consisting of O and S, and particular preferably are S, $R^1$-$R^{10}$ are independently of each other H, halogene, —CN, —NO₂ or a linear or branched, saturated or unsaturated $C_1$-$C_{40}$ hydrocarbon residue, which can be substituted 1- to 5-fold with halogen (F, Cl, Br, I), —OR$^a$, —NR$^a{}_2$, —CN and/or —NO₂, and wherein one or more CH₂-groups can be replaced by —O—, —S—, —NR$^b$—, —OC(O)— or —C(O)—, and wherein R$^a$ and R$^b$ are independently of each other H, $C_1$-$C_{30}$ akyl, $C_2$-$C_{30}$ alkenyl, $C_2$-$C_{30}$ alkynyl, $C_1$-$C_{30}$ haloalkyl, $C_2$-$C_{30}$ haloalkenyl, $C_2$-$C_{30}$ haloalkynyl or $C_2$-$C_{30}$ acyl.

Preferably, $R^1$, $R^2$, $R^5$ and $R^6$ are selected from the group consisting of H, halogen (F, Cl, Br, I), and a $C_{1-20}$ alkyl group.

Preferably, $R^3$, $R^4$ are selected from the group consisting of H, halogen (F, Cl, Br, I), and a $C_{1-20}$ alkyl group.

Preferably, $R^7$, $R^8$, $R^9$, $R^{10}$ are selected from the group consisting of H, halogen atom and $C_{1-20}$ alkyl groups.

It has been found that the phenacene compounds of the present invention have semiconducting activity. Materials prepared from these compounds have demonstrated unexpected properties. It has been discovered that compounds of the present invention can have high carrier mobility and/or good current modulation characteristics in field-effect devices (e.g., thin-film transistors). In addition, it has been discovered that compounds of the present invention can possess certain processing advantages compared to related representative compounds such as better solubility to permit solution-processability and/or good stability at ambient conditions, for example, air stability. Further, the compounds can be embedded with other components for utilization in a variety of semiconductor-based devices Preferred phenacene compounds are selected from compounds of formulae Ia-If:

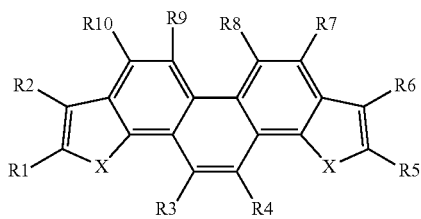

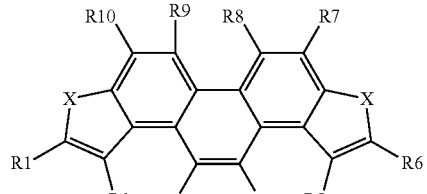

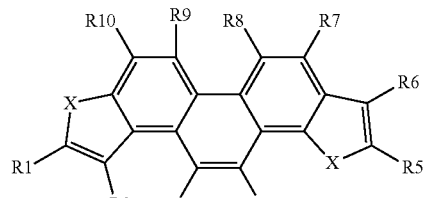

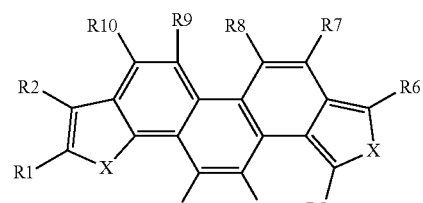

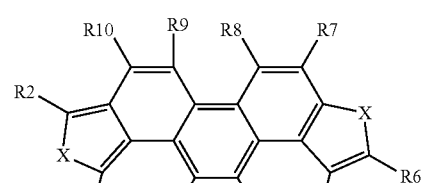

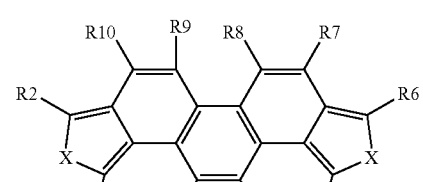

of which compound 1a is most preferred.

In a preferred embodiment, X is sulfur. The presence of sulfur can lead to additional intermolecular interaction via S—S interaction and can lead to higher mobility.

$R^1$-$R^{10}$ are independently of each other H, halogene, —CN, —NO₂ or a linear or branched, saturated or unsaturated $C_1$-$C_{40}$ hydrocarbon residue, which can be substituted 1- to 5-fold with halogen (F, Cl, Br, I), —OR$^a$, —NR$^a{}_2$, —CN and/or —NO₂, and wherein one or more CH₂-groups can be replaced by —O—, —S—, —NR$^b$—, —OC(O)— or —C(O)—, and wherein R$^a$ and R$^b$ are independently of each other H, $C_1$-$C_{30}$ akyl, $C_2$-$C_{30}$ alkenyl, $C_2$-$C_{30}$ alkynyl, $C_1$-$C_{30}$ haloalkyl, $C_2$-$C_{30}$ haloalkenyl, $C_2$-$C_{30}$ haloalkynyl or $C_2$-$C_{30}$ acyl.

Preferably, $R^1$-$R^{10}$ are independently of each other H, halogen, $C_1$-$C_{30}$ alkyl, $C_1$-$C_{30}$ alkoxy, $C_1$-$C_{30}$ alkylthio, $C_2$-$C_{30}$ alkenyl, $C_2$-$C_{30}$ alkynyl, $C_1$-$C_{30}$ haloalkyl, $C_2$-$C_{30}$ haloalkenyl or haloalkynyl, e.g. $C_1$-$C_{30}$ perfluoroalkyl or $C_2$-$C_{10}$ acyl. More preferably $R^1$-$R^{10}$ are independently of each other H, halogen, $C_1$-$C_{30}$ alkyl or $C_1$-$C_{30}$ alkoxy. Most preferably $R^1$-$R^{10}$ are independently of each other H, halogen or $C_1$-$C_{30}$ alkyl.

$C_1$-$C_{30}$ alkyl can be linear or branched, wherever possible.

Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl.

$C_1$-$C_{30}$ alkoxy groups are straight-chain or branched alkoxy groups, e.g. methoxy, ethoxy, n-propoxy, isopropoxy, n-butoxy, sec-butoxy, tert-butoxy, amyloxy, isoamyloxy, tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy or octadecyloxy.

The term "alkylthio group" means the same groups as the alkoxy groups, except that the oxygen atom of the ether linkage is replaced by a sulfur atom.

$C_2$-$C_{30}$ alkenyl groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or noctadec-4-enyl.

$C_2$-$C_{30}$ alkynyl is straight-chain or branched and may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-11-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_1$-$C_{30}$-perfluoroalkyl is a branched or unbranched group such as, for example, —$CF_3$, —$CF_2CF_3$, —$CF_2CF_2CF_3$, —$CF(CF_3)_2$, —$(CF_2)_3CF_3$ or —$O(CF_3)_3$.

The terms "haloalkyl, haloalkenyl and haloalkynyl" mean groups given by partially or wholly substituting the above mentioned alkyl group, alkenyl group and alkynyl group with halogen.

$C_2$-$C_{30}$ acyl is straight-chain or branched and may be saturated or unsaturated, such as, for example, ethanoyl, propanoyl, isobutanoyl, n-butanoyl, pentanoyl, hexanoyl, heptanoyl, octanoyl, nonanoyl, decanoyl or dodecanoyl.

Particularly preferred groups $R^1$, $R^2$, $R^5$ and $R^6$ are selected from H and a $C_{1-20}$ alkyl group.

Particularly preferred groups $R^3$, $R^4$ are selected from H and a $C_{1-20}$ alkyl group.

Particularly preferred groups $R^7$-$R^{10}$ are selected from H and a $C_{1-20}$ alkyl group.

In a preferred embodiment, $R^7$-$R^{10}$ are hydrogen.

In a further preferred embodiment, $R^3$ and $R^4$ are hydrogen.

In a still further preferred embodiment, one of $R^1$ and $R^2$ is hydrogen, and the other is a $C_{1-20}$ alkyl group, and one of $R^5$ and $R^6$ is hydrogen, and the other is a $C_{1-20}$ alkyl group.

Very preferred $C_{1-20}$ alkyl groups are $C_{10-20}$ alkyl groups.

Compounds of general formula I can be obtained by the synthetic route shown below.

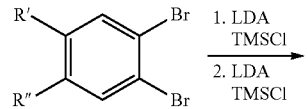

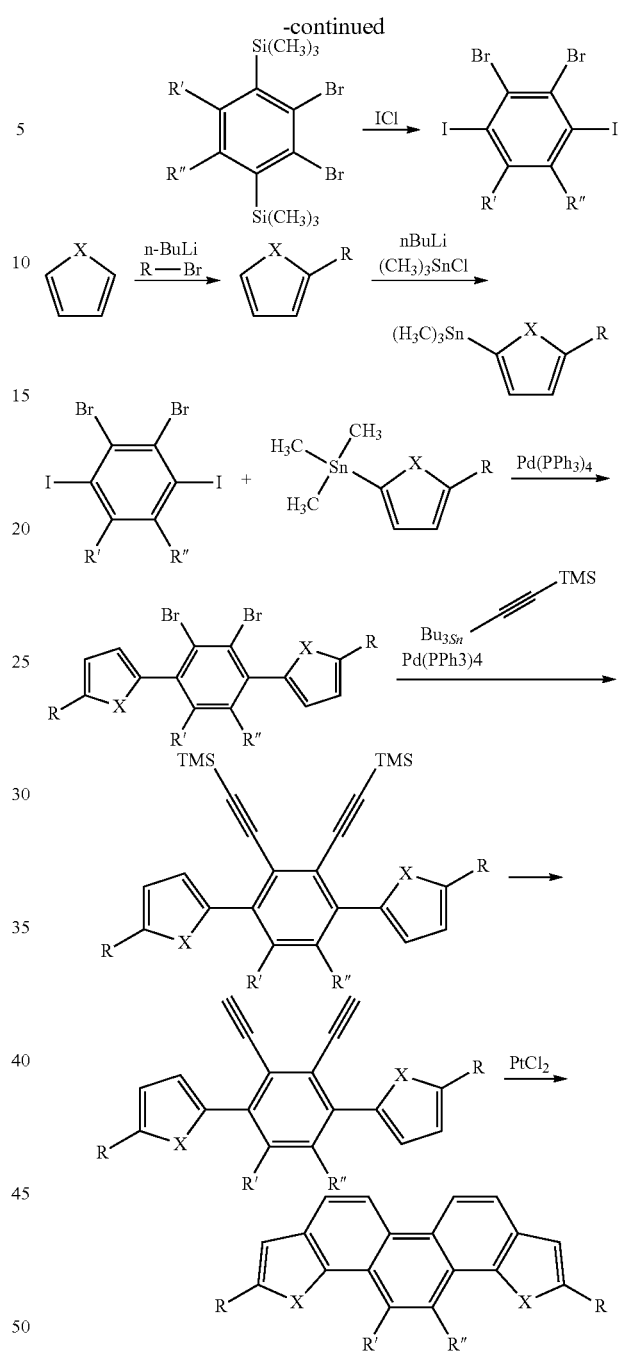

As the compounds disclosed herein are soluble in common solvents, the present invention can offer processing advantages in fabricating electrical devices such as thin film semiconductors, field-effect devices, organic light emitting diodes (OLEDs), organic photovoltaics, photodetectors, capacitors, and sensors. As used herein, a compound can be considered soluble in a solvent when at least 1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes;

acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methylpyrrolidone. Examples of common inorganic solvents include water and ionic liquids.

Accordingly, the present invention further provides compositions that include one or more compounds disclosed herein dissolved or dispersed in a liquid medium, for example, an organic solvent, an inorganic solvent, or combinations thereof (e.g., a mixture of organic solvents, inorganic solvents, or organic and inorganic solvents). In some embodiments, the composition can further include one or more additives independently selected from detergents, dispersants, binding agents, compatiblizing agents, curing agents, initiators, humectants, antifoaming agents, wetting agents, pH modifiers, biocides, and bactereriostats. For example, surfactants and/or other polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, such compositions can include one or more compounds disclosed herein, for example, two or more different compounds of the present invention can be dissolved in an organic solvent to prepare a composition for deposition. In certain embodiments, the composition can include two or more regioisomers. Further, it should be understood that the devices described herein also can comprise one or more compounds of the present invention, for example, two or more regioisomers as described herein.

Various deposition techniques, including various solution-processing techniques, have been used in preparing organic electronics. For example, much of the printed electronics technology has focused on inkjet printing, primarily because this technique offers greater control over feature position and multilayer registration. Inkjet printing is a non-contact process, which offers the benefits of not requiring a preformed master (compared to contact printing techniques), as well as digital control of ink ejection, thereby providing drop-on-demand printing. Micro dispensing is another non-contact method of printing. However, contact printing techniques have the key advantage of being well-suited for very fast roll-to-roll processing. Exemplary contact printing techniques include, but are not limited to, screen-printing, gravure printing, offset printing, flexographic printing, lithographic printing, pad printing, and microcontact printing. As used herein, "printing" includes a noncontact process, for example, inkjet printing, micro dispensing, and the like, and a contact process, for example, screen-printing, gravure printing, offset printing, flexographic printing, lithographic printing, pad printing, microcontact printing, and the like. Other solution processing techniques include, for example, spin coating, drop-casting, zone casting, dip coating, blade coating, or spraying. In addition, the deposition step can be carried out by vacuum vapor-deposition.

The present invention, therefore, further provide methods of preparing a semiconductor material. The methods can include preparing a composition that includes one or more compounds disclosed herein dissolved or dispersed in a liquid medium such as a solvent or a mixture of solvents, and depositing the composition on a substrate to provide a semiconductor material (e.g., a thin film semiconductor) that includes one or more compounds disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatiblizing agents, curing agents, initiators, humectants, antifoaming agents, wetting agents, pH modifiers, biocides, and bactereriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices such as field effect transistors (e.g., thin film transistors), photovoltaics, organic light emitting diodes (OLEDs), complementary metal oxide semiconductors (CMOSs), complementary inverters, D flip-flops, rectifiers, and ring oscillators, that make use of the compounds and the semiconductor materials disclosed herein also as well as methods of making the same are within the scope of the present invention.

Accordingly, the present invention provides articles of manufacture such as the various devices described herein that include a composite having a semiconductor material of the present invention, a substrate component, and/or a dielectric component. The substrate component can be selected from materials including doped silicon, an indium tin oxide (ITO), ITO-coated glass, ITO-coated polyimide or other plastics, aluminum or other metals alone or coated on a polymer or other substrate, a doped polythiophene or other polymers, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), self-assembled superlattice/self-assembled nanodielectric (SAS/SAND) materials (e.g., described in Yoon, M-H. et al., PNAS, 102 (13): 4678-4682 (2005), the entire disclosure of which is incorporated by reference herein), and hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be incorporated within various organic electronic, optical, and optoelectronic devices such as organic thin film transistors (OT-FTs), specifically, organic field effect transistors (OFETs), as well as sensors, capacitors, unipolar circuits, complementary circuits (e.g., inverter circuits), and the like.

An aspect of the present invention, therefore, relates to methods of fabricating an organic field effect transistor that incorporates a semiconductor material of the present invention. The semiconductor materials of the present invention can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

In certain embodiments, OTFT devices can be fabricated with the present compounds on doped silicon substrates, using $SiO_2$ as the dielectric, in top-contact geometries. In particular embodiments, the active semiconducting layer which incorporates at least a compound of the present invention can be deposited by vacuum vapor deposition at room temperature or at an elevated temperature. In other embodiments, the active semiconducting layer which incorporates at least a compound of the present invention can be applied by solution-based process, for example, spin-coating or jet printing. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a compound of the present invention can be deposited at room temperature or at an elevated temperature. In other embodiments, the active semiconducting layer which incorporates at least a compound of the present invention can be applied by spin-coating or printing as described herein. Gate and source/drain contacts can be made of Au, other metals, or conducting polymers and deposited by vapor-deposition and/or printing.

Other articles of manufacture in which compounds of the present invention are useful are photovoltaics or solar cells. Compounds of the present invention can exhibit broad optical absorption and/or a very positively shifted reduction potential making them desirable for such applications. Accordingly, the compounds described herein can be used as a p-type semiconductor in a photovoltaic design, which includes an adjacent n-type semiconducting material that forms a p-n junction. The compounds can be in the form of a thin film semiconductor, which can be a composite of the thin film semiconductor deposited on a substrate. Exploitation of compounds of the present invention in such devices is within the knowledge of the skilled artisan.

Accordingly, another aspect of the present invention relates to methods of fabricating an organic light-emitting transistor, an organic light-emitting diode (OLED), or an organic photovoltaic device that incorporates one or more semiconductor materials of the present invention.

The following examples are provided to illustrate further and to facilitate understanding of the present invention and are not in any way intended to limit the invention.

EXAMPLES 2,9-Dialkyl-1,10-dithiadicyclopenta[a,i]phenacene is Prepared by the Following Synthetic Route

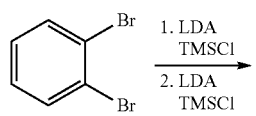

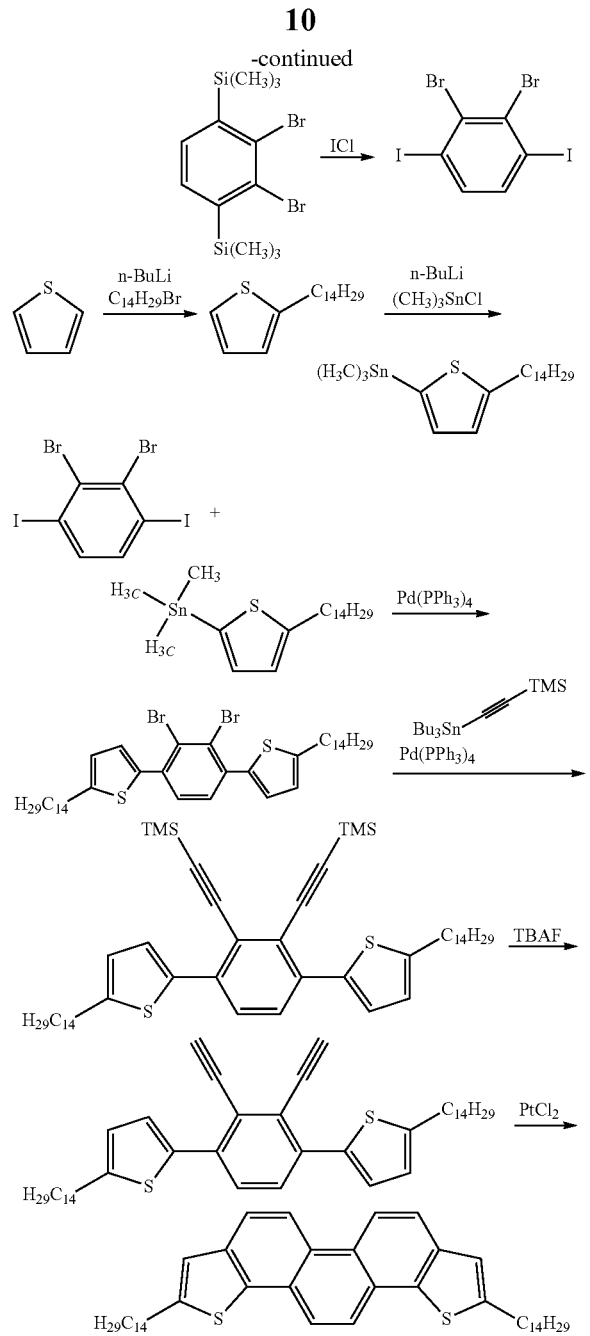

Example 1

Synthesis of 2,3-dibromo-1,4-bis-trimethylsilanyl-benzene

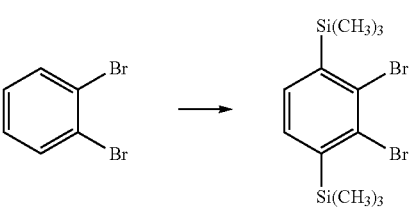

LDA (2 M, 70 mL, 140 mmol) was added dropwise to a solution of 1,2-dibromobenzene (15.0 g, 64 mmol) and chlorotrimethylsilane (20 mL, 153 mmol) in THF (90 mL) at −78° C. The resultant brown suspension was stirred at −78° C. for 30 min and then gradually warmed to room temperature. The reaction mixture was stirred for 18 h and then cooled to −78° C. again and chlorotrimethylsilane (20 mL, 153 mmol) was added. LDA (2M, 70 mL, 140 mmol) was added dropwise and the resultant brown suspension was stirred at −78° C. for 30 mins and then gradually warmed to room temperature. The reaction mixture was stirred for a further 18 h and then hydrolyzed with 1 N HCl (100 mL). The resultant mixture was extracted with diethyl ether (3×200 mL) and the combined organic layers was concentrated to give brown oil, which was used directly in the next step without further purification. $^1$H NMR (400 MHz, CDCl$_3$) δ 7.34 (s, 2H), 0.40 (18H).

Example 2

Synthesis of 2,3-dibromo-1,4-diiodo-benzene

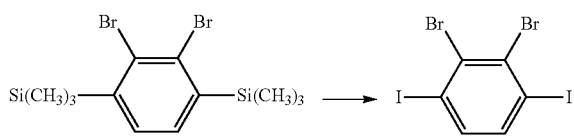

Iodine monochloride (1 M, 60 mL, 58 mmol) was added to a solution of 2,3-Dibromo-1,4-bis-trimethylsilanyl-benzene (10.0 g, 26.3 mmol) in dichloromethane (105 mL) at 0° C. The resultant purple solution was stirred at room temperature for 1 d. The reaction was cooled to 0° C. and additional iodine monochloride (1 M, 60 mL, 58 mmol) was added. The reaction mixture was stirred at room temperature for a further 1 d. Saturated sodium thiosulfate solution (150 mL) was added to the reaction mixture and extracted with dichloromethane (2×100 mL). The combined organic layers were concentrated to give a brown solid, which was purified by column chromatography on silica gel using 100% hexanes to yield a brown solid (8 g, 69%). Yield: 69%; Brown solid; $^1$H NMR (400 MHz, CDCl$_3$) δ 7.47 (s, 2H).

Example 3

Synthesis of 2-tetradecyl-thiophene

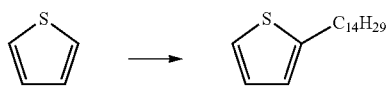

n-BuLi (1.6 M, 48 mL, 76 mmol) was added dropwise to a solution of thiophene (7.0 g, 83 mmol) in THF (70 mL) at −78° C. and stirred for 45 min. Tetradecyl bromide (23 mL, 76 mmol) in THF (25 mL) was added dropwise to the resultant suspension and then gradually warmed to room temperature and stirred for 18 h. The reaction mixture was quenched with water (60 mL) and extracted with diethyl ether (2×100 mL). The combined organic extracts were dried over MgSO$_4$ and concentrated to give brown oil (20.7 g, 97%), which was used directly in the next step without further purification. $^1$H NMR (400 MHz, CDCl$_3$) δ 7.10 (d, 1H, J=5.2 Hz), 6.91 (dd, 1H, J=5.7, 4.4 Hz), 6.77 (d, 1H, J=3.2 Hz), 2.82 (t, 2H, J=7.6 Hz), 1.68 (q, 2H, J=6.8 Hz), 1.50-1.20 (m, 22H), 0.88 (t, 3H, J=6.8 Hz).

Example 4

Synthesis of trimethyl-(5-tetradecyl-thiophen-2-yl)-stannane

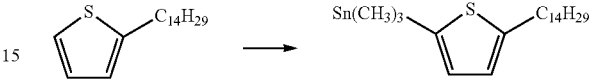

n-BuLi (1.6 M, 42 mL, 67 mmol) was added slowly to a solution of 2-tetradecyl-thiophene (17.0 g, 237 mmol) in THF (150 mL) at −78° C. and stirred for 30 min. Trimethyltin chloride (13.3 g, 67 mmol) in THF (30 mL) was added dropwise to the resultant suspension and then gradually warmed to room temperature. The reaction mixture was stirred for 18 h and quenched with saturated ammonium chloride solution (100 mL). The mixture was extracted with diethyl ether (2×100 mL) and the combined organic extracts were washed with brine (100 mL). The organic phase was dried and concentrated to give brown oil (26.8 g, 99%), which was used directly in the next step without further purification. $^1$H NMR (400 MHz, CDCl$_3$) δ 7.02 (d, 1H, J=3.2 Hz), 6.90 (d, 1H, J=3.2 Hz), 2.85 (t, 2H, J=8 Hz), 1.68 (q, 2H, J=7.6 Hz), 1.50-1.20 (m, 22H), 0.88 (t, 3H, J=6.8 Hz), 0.344 (s, 9H).

Example 5

Synthesis of 2,3-Dibromo-1,4-bis(trimethyl-(5-tetradecyl-thiophen-2-yl)-stannane)-benzene

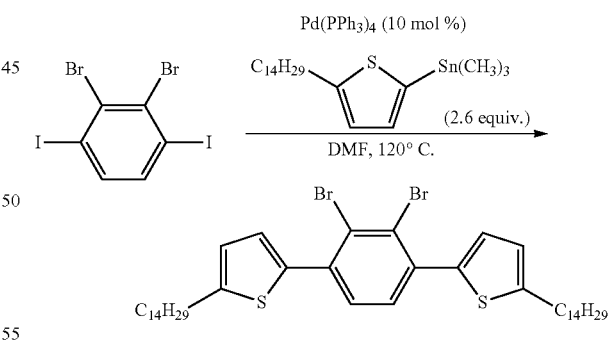

Tetrakis(triphenylphosphine)palladium(0) (3.55 g, 3.07 mmol) was added to a solution of 2,3-dibromo-1,4-diiodo-benzene (15.0 g, 30.7 mmol) and trimethyl-(5-tetradecyl-thiophen-2-yl)-stannane (35.0 g, 78.9 mmol) in DMF (100 mL) and stirred at 120° C. for 6 h. The reaction mixture was cooled to room temperature and diluted with water (100 mL). The mixture was extracted with dichloromethane (2×150 mL). The combined organic phases were dried and concentrated to give brown oil, which was purified by column chromatography to yield a white solid (15.0 g, 61%). $^1$H NMR (400 MHz, CDCl$_3$) δ 7.37 (s, 2H), 7.07 (d, 2H, J=3.6 Hz), 6.77 (d, 2H, J=3.6 Hz), 2.83 (t, 4H, J=7.6 Hz), 1.71 (q, 4H, J=6.8 Hz, 7.6 Hz), 1.50-1.20 (m, 44H), 0.88 (s, 6H).

Example 6

Synthesis of trimethyl-tributylstannanylethynyl-silane

n-BuLi (1.6 M, 24.4 mL, 39 mmol) was added dropwise to a solution of ethynyltrimethylsilane (4.0 g, 41 mmol) in THF (40 mL) at −78° C. and gradually warmed to 0° C. over 30 min. The reaction mixture was cooled to −78° C. again and tributyltin chloride (11.4 mL, 39 mmol) in THF (30 mL) was added dropwise to the resultant mixture. The reaction mixture was stirred for 18 h at room temperature and quenched with water (20 mL). The mixture was extracted with diethyl ether (2×100 mL) and the combined organic extracts were washed with brine (50 mL). The organic phase was dried and concentrated to give yellow oil (15.0 g, 95%), which was used directly in the next step without further purification. $^1$H NMR (400 MHz, CDCl$_3$) δ 1.67-1.45 (m, 6H), 1.45-1.20 (m, 6H), 0.98 (t, 6H, J=8.4 Hz), 0.90 (t, 9H, J=7.2 Hz), 0.16 (s, 9H).

Example 7

Synthesis of 2,3-Bis(ethynyltrimethylsilane)-1,4-bis(trimethyl-(5-tetradecyl-thiophen-2-yl)-stannane)-benzene

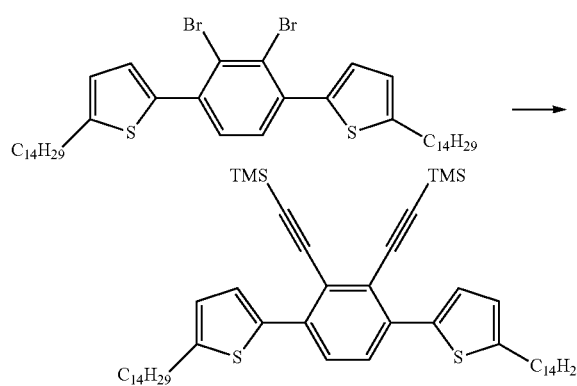

Tetrakis(triphenylphosphine)palladium(0) (2.9 g, 2.52 mmol) was added to a solution of 2,3-dibromo-1,4-bis(trimethyl-(5-tetradecyl-thiophen-2-yl)-stannane)-benzene (10.0 g, 12.6 mmol) and trimethyl-tributylstannanylethynyl-silane (14.6 g, 37.8 mmol) in toluene (250 mL) and stirred at 120° C. for 5 h. The reaction mixture was cooled to room temperature and diluted with water (100 mL). The mixture was extracted with dichloromethane (2×100 mL). The combined organic phases were dried and concentrated to give brown oil, which was purified by flash column chromatography to yield yellow solids (14.5 g) as crude product in quantitative yield. The crude product was used directly in the next step without further purification. $^1$H NMR (400 MHz, CDCl$_3$) δ 7.49 (d, 2H, J=3.6 Hz), 7.42 (s, 2H), 6.74 (d, 2H, J=3.6 Hz), 2.82 (t, 4H, J=7.6 Hz), 1.80-1.60 (m, 4H), 1.50-1.20 (m, 44H), 0.92 (t, 6H, J=7.6 Hz), 0.27 (s, 18H).

Example 8

Synthesis of 2,3-diethynyl-1,4-bis(trimethyl-(5-tetradecyl-thiophen-2-yl)-stannane)-benzene

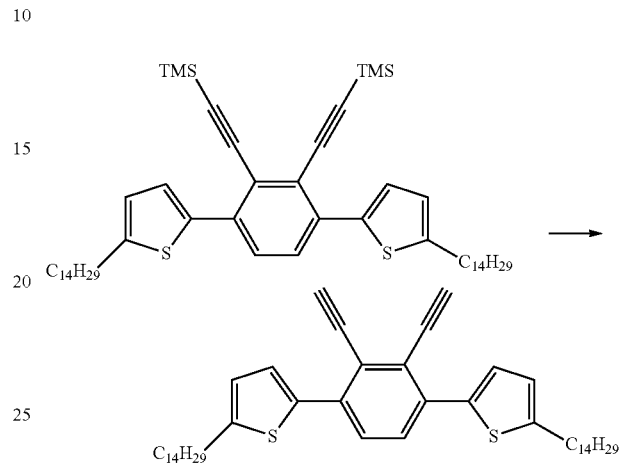

Tetrabutylammonium fluoride in THF solution (1 M, 83 mL, 83 mmol) was added dropwise to a solution of 2,3-Bis(ethynyltrimethylsilane)-1,4-bis(trimethyl-(5-tetradecyl-thiophen-2-yl)-stannane)-benzene (20.9 g, 25 mmol) in THF (240 mL) at room temperature and stirred for 3 h. The reaction mixture was quenched with saturated ammonium chloride solution (200 mL) and extracted with THF (3×100 mL). The combined organic phases were dried and concentrated to give a brown solid, which was purified by flash column chromatography to yield a pale yellow solid (9.5 g, 55% over 2 steps). $^1$H NMR (400 MHz, CDCl$_3$) δ 7.48 (d, 2H, J=3.6 Hz), 7.45 (s, 2H), 6.77 (d, 2H, J=3.6 Hz), 3.54 (s, 2H), 2.82 (t, 4H, J=7.6 Hz), 1.80-1.60 (m, 4H), 1.50-1.20 (m, 44H), 0.91 (t, 6H, J=7.6 Hz).

Example 9

Synthesis of 2,9-ditetradecyl-1,10-dithia-dicyclopenta[a,i]phenanthrene

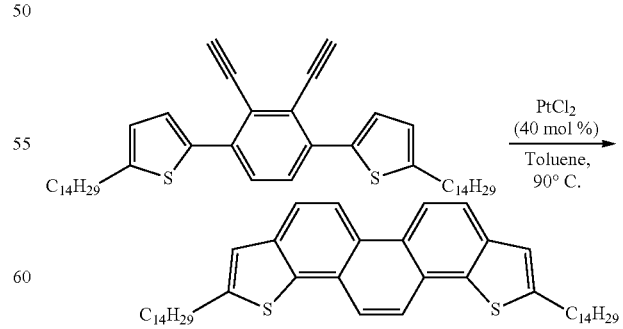

A solution of 2,3-diethynyl-1,4-bis(trimethyl-(5-tetradecyl-thiophen-2-yl)-stannane)-benzene (8.9 g, 13 mmol) and platinum dichloride (1.4 g, 5.21 mmol) in toluene (40 mL) was stirred at 90° C. for 18 h. The reaction mixture was cooled to room temperature and filtered. The filtrate was concentrated and the residue was treated with hexanes (50 mL). The resultant brown suspension was filtered and the crude product isolated as a brown residue. The brown residue was recrystallized from hot hexanes to yield an off-white solid (1.6 g, 18%). $^1$H NMR (400 MHz, CDCl$_3$) δ 8.61 (d, 2H, J=8.8 Hz), 8.08 (s, 2H), 7.88 (d, 2H, J=8.8 Hz), 7.17 (s, 2H), 2.99 (t, 4H, J=7.2 Hz), 1.85-1.75 (m, 4H), 1.50-1.20 (m, 44H), 0.87 (t, 6H, J=7.2 Hz).

Example 10

General procedure for device fabrication of bottom-gate top-contact OFETs

Highly doped p-type silicon (100) wafers with a 200 nm-thick thermally grown silicon dioxide (SiO$_2$) were used as substrates. A semiconductor layer was fabricated by either solution- or vacuum-deposition (<1×10$^{-3}$ Pa) technique. Then a 50 nm-thick of Au layer for source and drain electrodes was deposited though a shadow mask to give top-contact OFET devices. The channel width (W) was 50 μm and channel length (L) was 1000 μm typically.

The electrical characteristics of the transistors were measured on a Keithley 4200 SCS. All measurements were performed in air at room temperature. All the OFETs based on phenacene derivative showed typical p-type characteristics. To obtain the transfer curve the drain-source voltage (V$_d$) was held to −60 V. The charge-carrier mobility for hole (μ) was extracted in the saturation regime from the slope of $(I_d)^{1/2}$ versus V$_g$ and the threshold voltage (V$_{th}$) using the following equation; $\mu = 2 I_d/\{(W/L)C_i(V_g - V_{th})^2\}$. The performances of the OFETs are summarized in Table 1 and FIGS. 1 and 2.

Figure 1B:
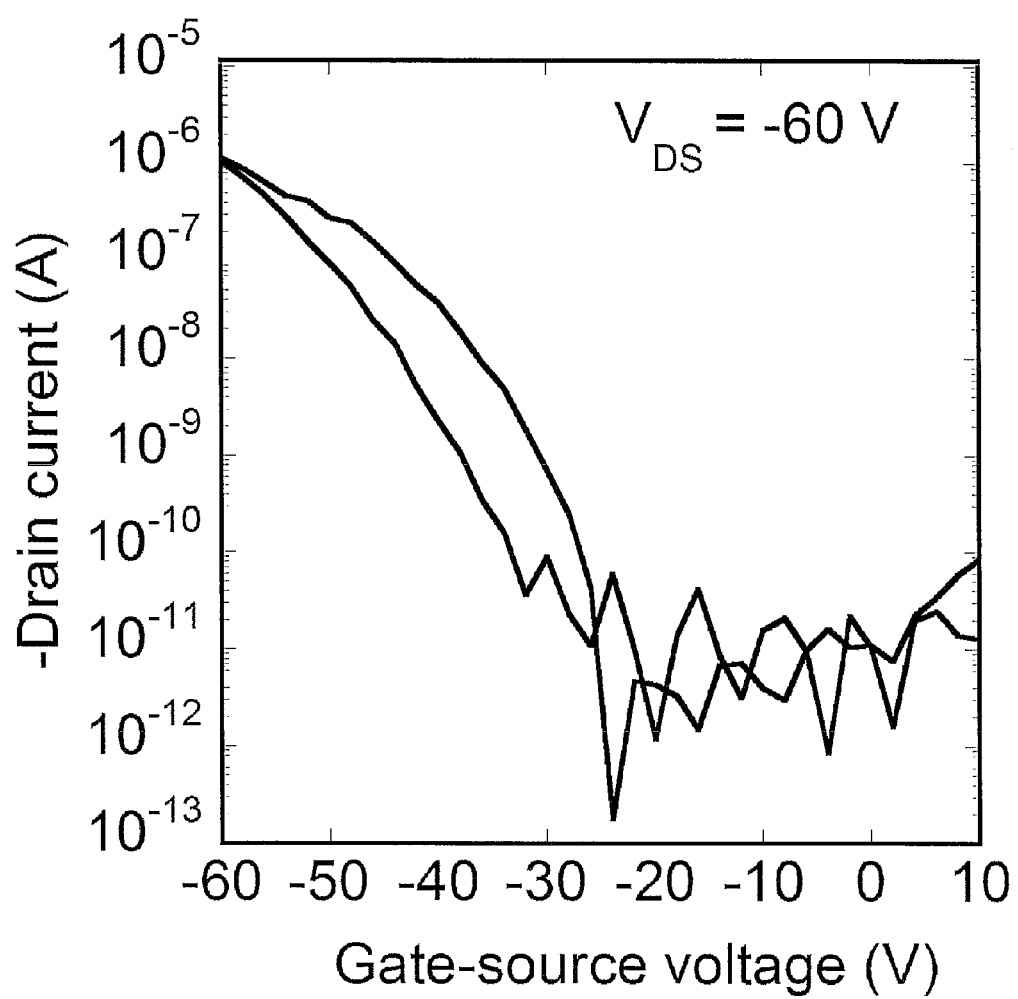

FIGS. 1A and B show output and transfer characteristics of solution-deposited OFETs. In FIG. 1A, the drain current is plotted against the drain voltage. In FIG. 1B, the drain current is plotted against the gate-source voltage.

Figure 2:
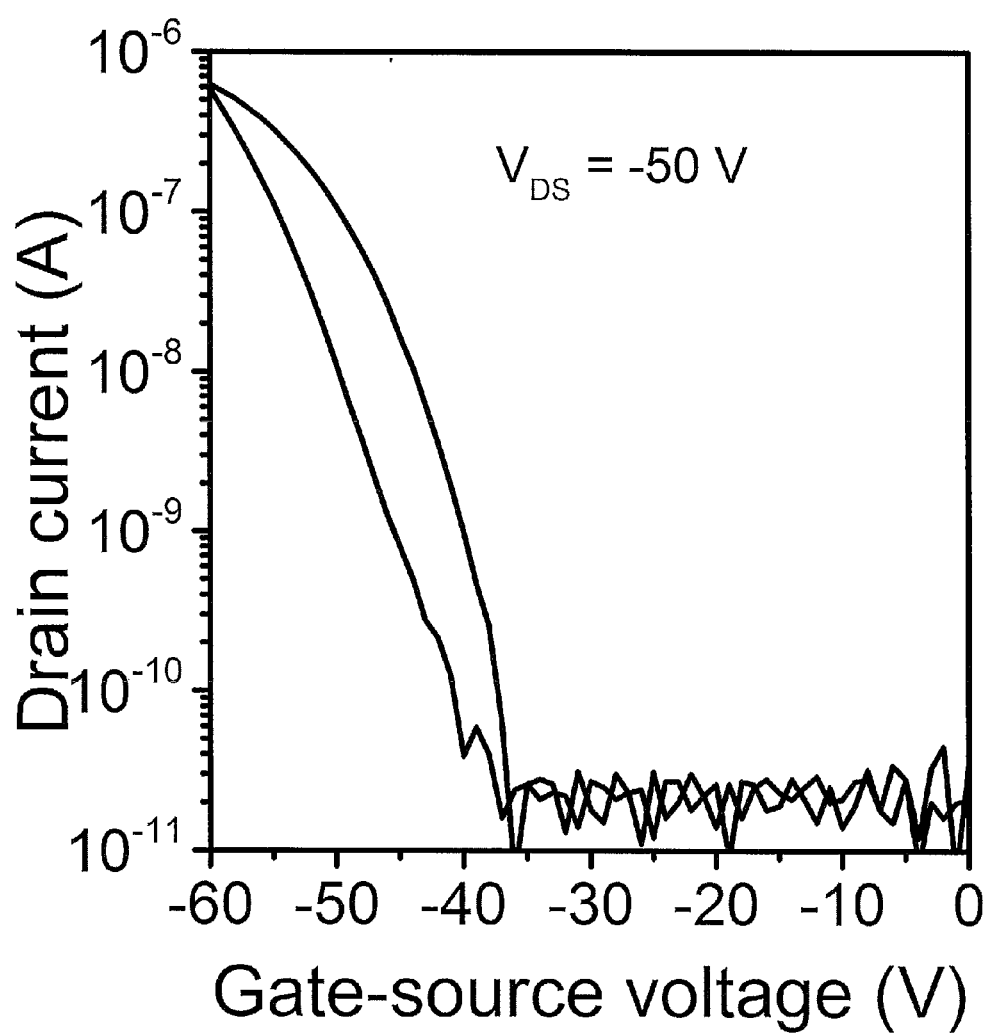

FIG. 2 shows transfer characteristics of vacuum-deposited OFETs. the drain current is plotted against the gate-source voltage.

TABLE 1

Typical characteristics of OFETs based on phenacene.

| process | V$_{th}$/V | μ/cm$^2$V$^{-1}$s$^{-1}$ | I$_{on}$/I$_{off}$ |
|---------|-----------|--------------------------|---------------------|
| solution | −40 | 0.03 | 10$^4$ |
| vacuum | −30 | 0.19 | 10$^5$ |

The invention claimed is:
1. Phenacene compounds of formula I

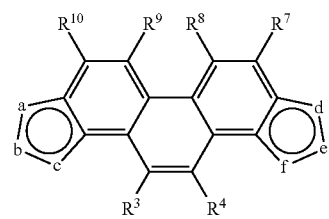

(I)

wherein
one of groups a, b and c is X and the other two groups are C—R$^1$ and C—R$^2$, respectively,
one of groups d, e and f is X and the other two groups are C—R$^5$ and C—R$^6$, respectively,
wherein X are, independently of each other, selected from the group consisting of O, S and Se,
R$^1$-R$^{10}$ are independently of each other H, halogene, —CN, —NO$_2$ or a linear or branched, saturated or unsaturated C$_1$-C$_{40}$ hydrocarbon residue, which can be substituted 1- to 5-fold with halogen (F, Cl, Br, I), —OR$^a$, —NR$^a_2$, —CN and/or —NO$_2$, and wherein one or more CH$_2$-groups can be replaced by —O—, —S—, —NR$^b$—, —OC(O)— or —C(O)—, and wherein R$^a$ and R$^b$ are independently of each other H, C$_1$-C$_{30}$ akyl, C$_2$-C$_{30}$ alkenyl, C$_2$-C$_{30}$ alkynyl, C$_1$-C$_{30}$ haloalkyl, C$_2$-C$_{30}$ haloalkenyl, C$_2$-C$_{30}$ haloalkynyl or C$_2$-C$_{30}$ acyl.

2. Phenacene compounds according to claim 1 of formulae Ia-If

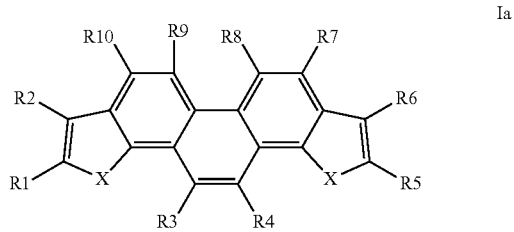

Ia

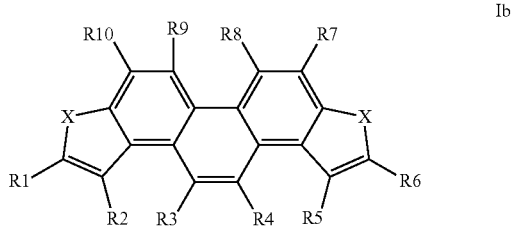

Ib

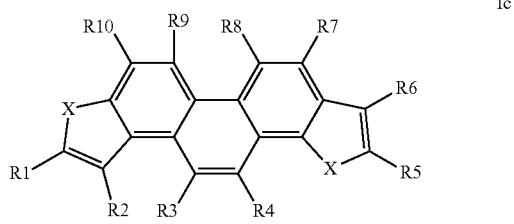

Ic

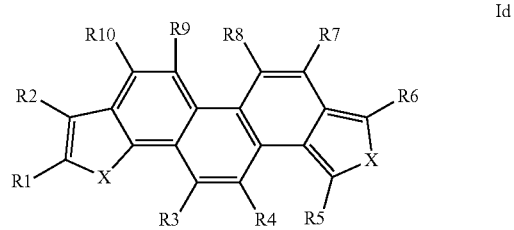

Id

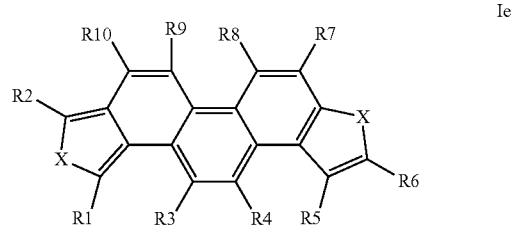

Ie

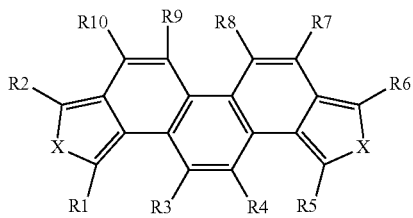

wherein

X and $R^1$-$R^{10}$ are as defined in claim 1.

3. Phenacene compounds according to claim 1, wherein X is O.

4. Phenacene compounds according to claim 1, wherein X is S.

5. Phenacene compounds according to claim 1, wherein $R^7$-$R^{10}$ are hydrogen.

6. Phenacene compounds according to claim 1, wherein $R^3$ and $R^4$ are hydrogen.

7. Phenacene compounds according to claim 1, wherein $R^1$, $R^2$, $R^5$ and $R^6$ are independently of each other hydrogen or a $C_{1-20}$ alkyl group.

8. Phenacene compounds according to claim 2 of formula Ia, wherein X is S, $R^1$ and $R^5$ are a $C_{1-20}$ alkyl group and $R^2$-$R^4$ and $R^6$-$R^{10}$ are hydrogen.

9. A thin film semiconductor comprising one or more compounds of claim 1.

10. A field effect transistor device comprising the thin film semiconductor of claim 9.

11. A photovoltaic device comprising the thin film semiconductor of claim 9.

12. An organic light emitting diode device comprising the thin film semiconductor of claim 9.

13. A unipolar or complementary circuit device comprising the thin film semiconductor of claim 9.

14. Phenacene compounds according to claim 1, wherein X is Se.

15. Phenacene compounds according to claim 1, wherein said $R^1$-$R^{10}$ are independently of each other selected from the group consisting of H, halogene, $C_1$-$C_{30}$ alkyl, $C_1$-$C_{30}$ alkoxy, $C_1$-$C_{30}$ alkylthio, $C_1$-$C_{30}$ alkenyl, $C_2$-$C_{30}$ alkynyl, $C_1$-$C_{30}$ haloalkyl, $C_2$-$C_{30}$ haloalkenyl, and $C_2$-$C_{30}$ haloalkynyl.

16. Phenacene compounds according to claim 1, wherein said $R^1$-$R^{10}$ are independently of each other selected from the group consisting of H, halogen, $C_1$-$C_{30}$ alkyl and $C_1$-$C_{30}$ alkoxy.

17. Phenacene compounds according to claim 1, wherein said $R^1$-$R^{10}$ are independently of each other selected from the group consisting of H, halogen, and $C_1$-$C_{30}$ alkyl.

* * * * *